United States Patent
Hansen et al.

(10) Patent No.: US 8,335,562 B2
(45) Date of Patent: Dec. 18, 2012

(54) AUTOMATED EXTERNAL DEFIBRILLATOR (AED) WITH CONTEXT-SENSITIVE HELP

(75) Inventors: Kim Hansen, Renton, WA (US); Kurt Fischer, Lynnwood, WA (US); James A. Froman, Issaquah, WA (US); Seiya Ohta, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 972 days.

(21) Appl. No.: 12/264,396

(22) Filed: Nov. 4, 2008

(65) Prior Publication Data
US 2009/0054939 A1 Feb. 26, 2009

Related U.S. Application Data

(63) Continuation of application No. 10/675,156, filed on Sep. 30, 2003, now abandoned.

(51) Int. Cl.
*A61N 1/00* (2006.01)
(52) U.S. Cl. .......................................................... 607/5
(58) Field of Classification Search .................. 607/4–6, 607/142
See application file for complete search history.

(56) References Cited

U.S. PATENT DOCUMENTS

| | | |
|---|---|---|
| 2002/0143366 A1 | 10/2002 | Herleikson |
| 2003/0083699 A1 | 5/2003 | Hamilton et al. |
| 2005/0070964 A1 | 3/2005 | Hansen et al. |

*Primary Examiner* — Mark W Bockelman
(74) *Attorney, Agent, or Firm* — W. Brinton Yorks, Jr.

(57) ABSTRACT

A defibrillator system is disclosed including an operational state input, a user-operated information request input, and a user guidance output. The defibrillator system can be implemented as an AED, a manual defibrillator, or as a defibrillator trainer. The defibrillator system further utilizes the state and request inputs to determine a context-sensitive rescue information which is provided to the output.

20 Claims, 3 Drawing Sheets

AUTOMATED EXTERNAL DEFIBRILLATOR (AED) WITH CONTEXT-SENSITIVE HELP

BACKGROUND OF THE INVENTION

Automated External Defibrillators (AEDs) have been available for public use for several years, and have proven effective at treating Sudden Cardiac Arrest (SCA). SCA kills about 250,000 Americans a year and is the leading cause of death in the U.S. Untreated SCA usually results in death in a very short time, and survival rates for SCA decline by about 10% for every minute defibrillation treatment is delayed. Because most EMS or other medical response cannot reach the scene of SCA within a very few minutes, it is important for witnesses or bystanders to be able to apply defibrillation treatment as quickly as possible, whenever a defibrillator is available.

Cardiopulmonary resuscitation (CPR) is often performed concurrent with AED use. CPR is a combination of artificial respiration and artificial circulation that keeps oxygenated blood flowing to the brain during cardiac arrest. The effectiveness of CPR is highly dependent on the proficiency of the rescuer's application, and as such, the AHA and American Red Cross have established detailed step-by-step CPR procedures. Many people receive CPR training each year, but most, even emergency responders, have not maintained their proficiency. Rescuers may find it difficult to recall these procedures, especially during high stress rescue situations and as standards evolve.

Similarly, successful defibrillation requires the rescuer to perform a specific sequence of steps in order for the AED to function properly. The rescuer must activate the AED, remove interfering clothing from the victim's torso, successfully apply the defibrillation electrode pads in their proper locations on the torso, and cause the defibrillation shock to be delivered in order to defibrillate the heart. The victim's chance of survival improves greatly the faster these steps are completed.

AEDs are increasingly being deployed into environments where a minimally-trained or untrained user is likely to be the first responder. AEDs now appear in businesses, schools, public venues and homes in addition to the more traditional emergency responder, ambulance and rescue squad environments.

The problems of minimal training, high levels of stress accompanied by noise and confusion, and a very limited time in which to effect a rescue negatively affects the chances of a successful rescue. The rescue of an SCA victim is a high stress event. In order to keep the rescuer on track during the stress of a rescue, many AEDs guide the user through the defibrillation process with audible or visual prompts. These prompting features are very useful to a user who is unfamiliar with the defibrillation procedure or with CPR protocol. An example of a defibrillator with automatic CPR prompting features is described in U.S. Pat. No. 6,356,785 by Snyder et al., titled "External Defibrillator with CPR Prompts and ACLS Prompts and Methods of Use", which is incorporated herein.

On the other hand, the same prompting features can delay a proficient rescuer who is able to work faster than the prompts, or can complicate the already chaotic rescue situation with extraneous and distracting information. In some cases, the continuing prompting noise may tempt a rescuer to turn the AED off when a perceived "safe" time in the rescue is reached. If the SCA recurs, the AED then would not have the ability to sense or respond to the recurring emergency.

Thus, there is a need for an AED which provides appropriate information only when it is needed, with minimal action by the user. Specifically, what is needed is an improved AED which selectively provides rescue information to the user in order to reduce confusion and improve the guidance for successful cardiac rescue. Further, an improved AED which can dynamically alter the guidance provided to the rescuer based on both the state of the rescue and on whether or not the rescuer has requested guidance during that rescue state could improve the chances of a successful SCA treatment.

SUMMARY OF THE INVENTION

The apparatus and methods of the present invention are the result of the inventors' discovery that the interaction between defibrillator and user is significantly enhanced by dynamically modifying the sestet of rescue information based on the progress of the rescue. The present inventors have further discovered that a user improves the likelihood of performing a successful rescue if the user retains some control over the delivery of the guidance; i.e. the help prompting should be optional and not completely automatic. With appropriate optional guidance, the user eliminates the stress associated with extraneous noise and distraction, while simultaneously retaining the ability to quickly obtain assistance if the user becomes confused during the rescue. In addition, optional guidance reduces the likelihood that the AED is turned off mid-rescue in an attempt to reduce stress and distraction. The AED of the present invention will remain quiet unless conditions or a request actually warrant a prompt.

It was further discovered that defibrillator users prefer an information request input that is dedicated and distinct from other elements in the AED user interface. This discovery was not obvious to those skilled in the AED art because it was previously assumed that an AED should minimize the number of knobs and switches in order to simplify use. The result of this discovery was that the addition of another button for information request, preferably a flashing button, enhances the likelihood of successful use, even for minimally trained users, and is worth any additional "clutter" that may be caused by the additional button. Still, it is important to design the information request button such that distraction of the operator is minimized, particularly when there is no additional information to be gained by pressing the button.

In accordance with these discoveries, the present invention is directed to an improved defibrillator system comprising an operational state input, a user-operated information request input, and a user guidance output. The defibrillator system can be implemented as an AED, a manual defibrillator, or as a defibrillator trainer. The defibrillator system further utilizes the state and request inputs to determine a context-sensitive rescue information which is provided to the output. The preferred embodiment of the request input is a button on the AED. The button may be illuminated when active to further assist the user in locating it. Output rescue information may be provided through a speaker with verbal instructions or audible signals without requiring a display screen. Optionally, the rescue information may be provided visually through a display screen or other dynamic visual indicators such as LEDs, pictograms, or iconic representations.

Another embodiment of the present invention is directed to the above-described defibrillator system with an additional electrode interface input indicating the presence of a patient electrode, and if present, the type of electrode. Exemplary electrode types include rescue electrodes, training electrodes, pacing electrodes, monitoring electrodes and cardioversion electrodes. Rescue electrodes may further be distinguished as adult or pediatric electrodes. Electrodes of all configurations may also be hereafter referred to as "electrode pads" or "pads".

Yet another embodiment of the present invention is a method of providing context-sensitive rescue information to the user of a defibrillator system which depends upon both the operational state of the system and an information request input. Examples of context-sensitive rescue information are: defibrillator condition (including whether pediatric electrodes are installed); defibrillation procedure guidance; user reassurance comments; enhanced CPR guidance; defibrillator training scenario guidance; and defibrillator administrative guidance. The method may further comprise the step of sensing the presence and type of patient electrode attached to the defibrillator, and wherein the context-sensitive rescue information is selected based on the electrode presence/type input.

Other features, attainments, and advantages will become apparent to those skilled in the art upon a reading of the following description when taken in conjunction with the accompanying drawings.

DETAILED DESCRIPTION OF THE INVENTION

Figure 1:
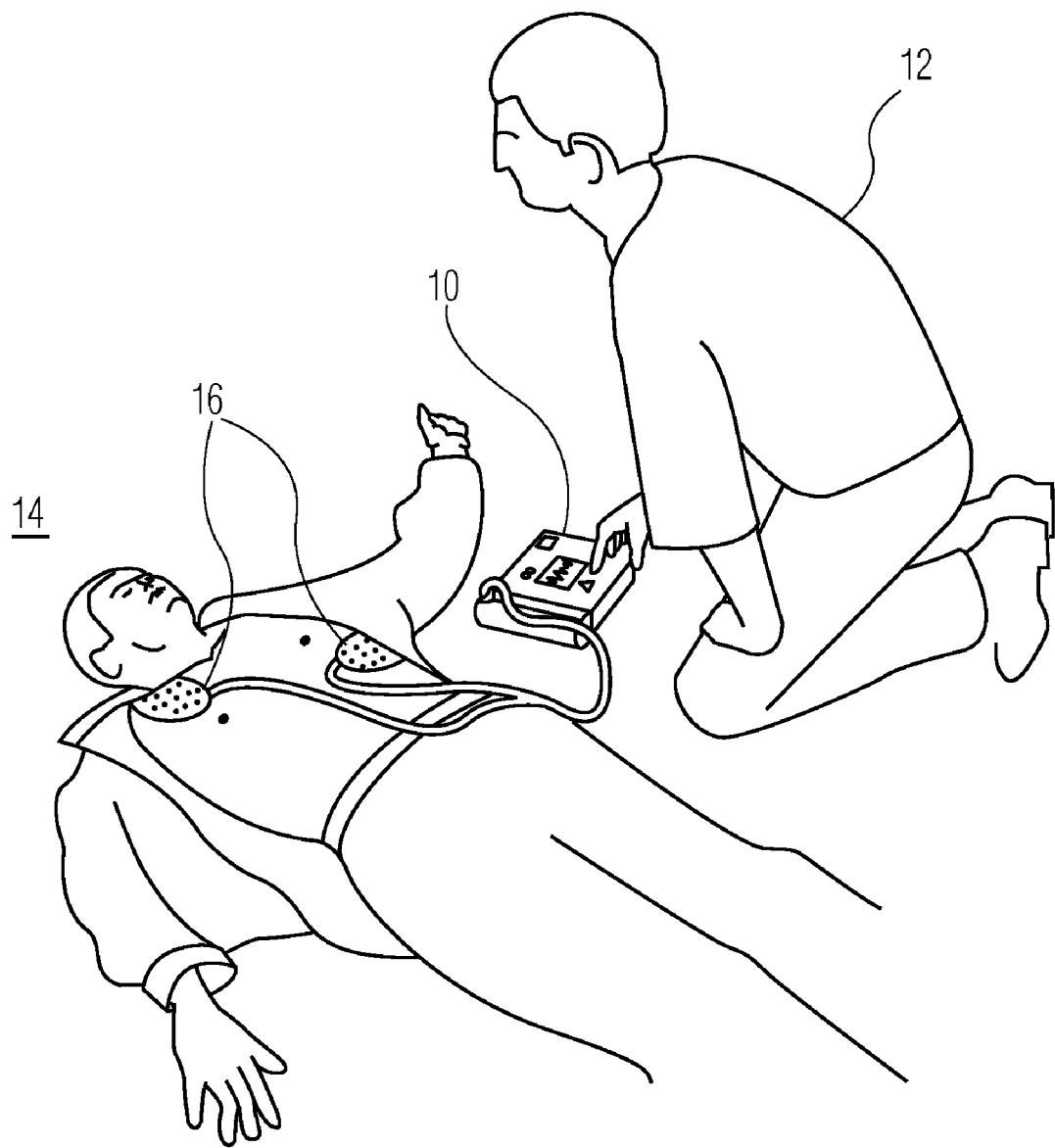
FIG. 1 is a diagram of a prior art AED being used during the rescue of a cardiac victim.

The defibrillation of a SCA victim using an automatic external defibrillator of the prior art is illustrated in. FIG. 1. The rescuer 12 begins the process by connecting an AED 10 to the victim 14 via a set of AED electrodes 16 which are attached to the victim as shown. The rescuer 12 activates the AED 10, which in turn analyzes the patient 14 cardiac parameters through the AED 25 electrodes 16. If the cardiac parameters indicate that the victim is in ventricular fibrillation (VF), the AED 10 will prompt the rescuer 12 to remain clear of the patient and press the triangular shock button to initiate a patient shock through the electrodes 16. The cardiac parameters and prompts may be displayed visually on the AED screen as shown.

If the defibrillation shock is successful at restoring normal cardiac rhythm, the AED 10 will so indicate and will further prompt the rescuer 12 to perform other first aid actions. If the shock is unsuccessful, the AED 10 may repeat the cardiac analysis and shock sequence, or may prompt the user 12 to begin CPR. The prompting sequence in the prior art AED 10 follows a pre-programmed script, which in very basic AEDs, advances based upon elapsed time. In later generation devices, the script advances based on a detected status of the patient, as detected by signals from the patient electrodes. In addition, AED 10 may provide generic CPR instructions during the CPR period. The prompts are generally provided audibly, or can optionally be provided by text messages on an electronic display.

Figure 2:
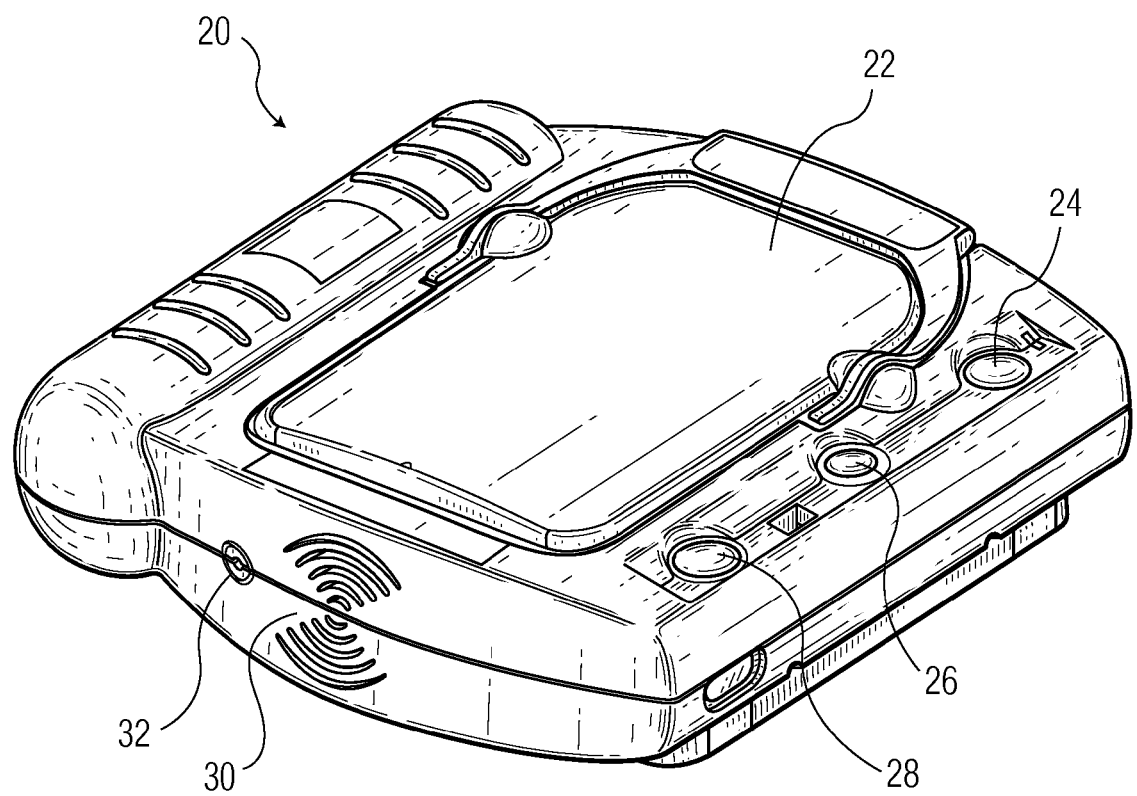
FIG. 2 illustrates an AED of the present invention, with a button embodiment of the user request input.

FIG. 2 shows one embodiment of the present invention. AED 20 comprises a set of patient electrodes that are stored inside cartridge 22. Activation of AED 20 may be through an on/off button 24 or by removing the protective electrode cartridge cover 22. The electrodes are removed from cartridge 22 and applied to the patient's bare torso, the detection of which automatically begins the analysis of the patient's condition. When indicated, a shock button 28 is pressed to deliver a defibrillation shock. AED 20 lacks the visual display of the prior art AED 10 in order to reduce cost, size, weight and complexity in the device.

FIG. 2 further illustrates the dedicated user information request button 26 on AED 20. The information request button 26 serves as the primary interface between rescuer 12 and AED 20. Information request button 26 may be selectively activated by the AED 20 and illuminated to indicate that information is available during that particular operational state. The illumination feature thus serves to draw the user's attention to the information request button 26 only during appropriate situations. By keeping the information request button dark when it is not appropriate to press it, user distraction is minimized.

When the rescuer 12 presses the information request button 26, AED 20 issues help information based on the operational state of the device. By coupling the delivered information based to the operational state of the device, the device is able to provide information that is appropriate to the context in which it was requested. Thus, the provided information is "context-sensitive". In the preferred embodiment, the context-sensitive help is audibly conveyed through speaker 30 or through buzzer 32. Visual help may optionally be displayed (not shown). One exemplary type of context-sensitive help is a detailed set of CPR instructions, provided only if the information button is pressed during a CPR period.

Figure 3:
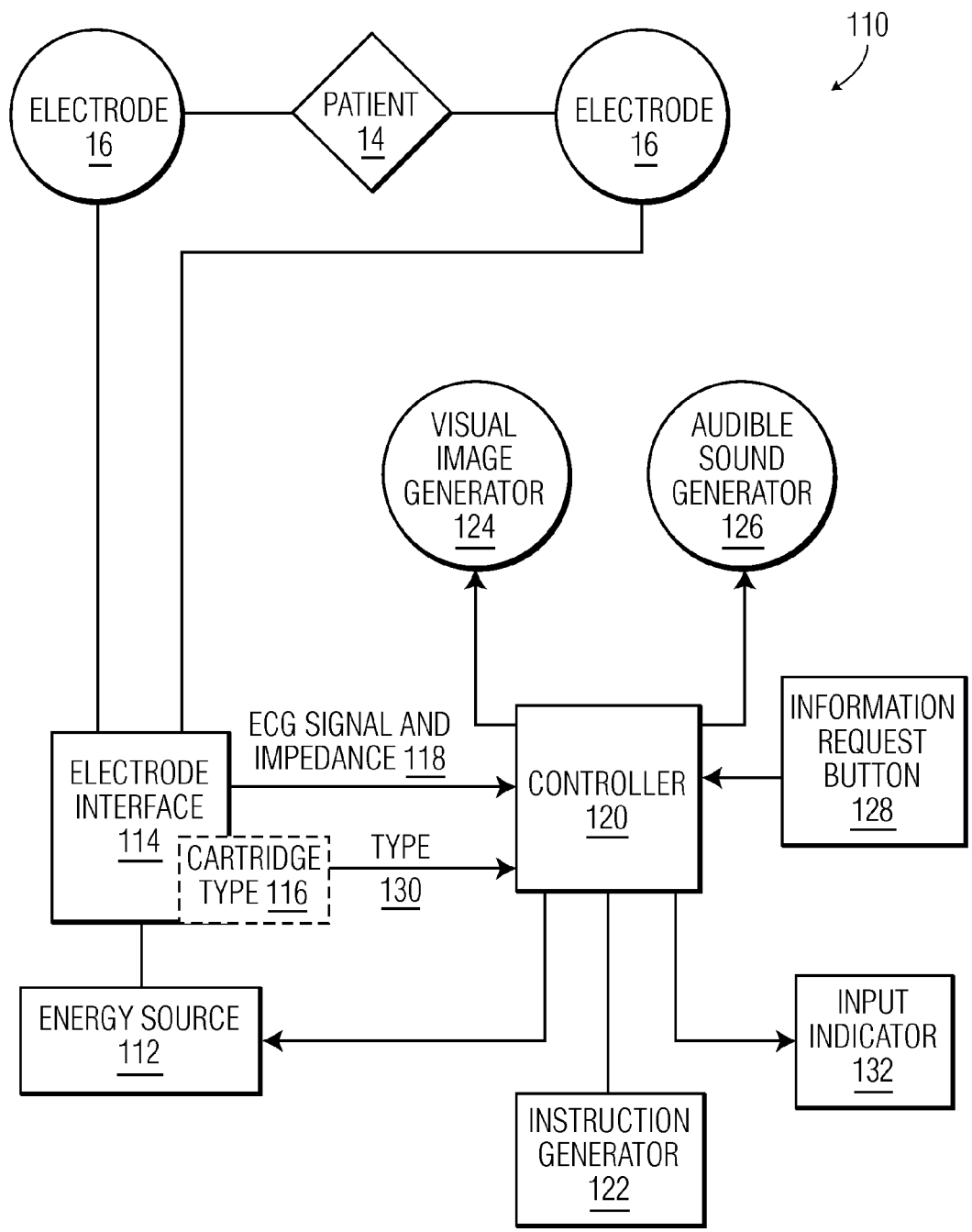
FIG. 3 is a block diagram of one embodiment of the inventive AED apparatus.

FIG. 3 is a schematic block diagram of a defibrillator system 110 according to a preferred embodiment of this invention. The defibrillator system 110 comprises an energy source 112 to provide a defibrillating shock to the patient 14 via electrode interface 114 and electrodes 16. Defibrillator system 110 may be implemented as a manual defibrillator, an AED, or a defibrillator trainer that simulates the behavior of a manual defibrillator or AED in use.

A controller 120 operates electrode interface 114 to selectively connect and disconnect energy source 112 to electrodes 16 in order to provide electrotherapy to the patient 14. Controller 120 also controls the information flow from an instruction generator 122 to the user via a sound generator 126 or visual indicator or image generator 124. Instruction generator 122 may also activate protocol changes being performed by the defibrillator 110 based on information received from the controller 120. For example, controller 120 may sense how the AED 110 has been activated, either with on/off button 24 or by removing the electrode cartridge cover 22, to determine which protocol to follow. Output of the selected instruction protocol is then accomplished through sound generator 126 and speaker 30 or buzzer 32. Audible commands may include verbal commands directing the rescuer in the proper sequence and timing for administering CPR or ACLS, or audible timing tones, such as those generated by a metronome, for timing the administration of CPR. Optionally, output may be passed through visual image generator 124 to an LCD display (not shown) for displaying or highlighting textual and graphical instructions.

Controller 120 controls the information flow to the sound generator 126 or visual image generator 124 based on parameters that indicate the operational state of the defibrillator. Controller 120 further comprises an internal memory for storing operational state information and a timing circuit for determining the elapsed time between successive operational states or between successive user inputs. Operational state parameters are provided from electrode interface 114. Parameters passed from electrode interface 114 to controller 120 comprise patient ECG signals and electrode-to-electrode impedance measurements. Optionally, electrode interface 114 detects and passes to controller 120 information on whether an electrode cartridge 22 is installed and if so, what type of electrode cartridge 22 is installed. Exemplary electrode cartridge types are: ADULT, PEDIATRIC, and TRAINING cartridges.

Controller 120 further controls user information flow based on the state of a user-operated information request button 128. Information request button 128 states may be as simple as PRESSED or NOT PRESSED. In an alternate embodiment, information request button 128 states comprise: PRESSED FOR <2 SECONDS, PRESSED FOR >2 SECONDS, PRESSED FOR >4 SECONDS.

Other embodiments of the invention are contemplated in which controller 120 controls the state of the information request button 128 itself through an input indicator 132. To indicate that information request button 128 is active, indicator 132 causes the information request button 128 to illuminate, alerting the user that information is available at that particular operational state by pressing the button 128. The illumination feature thus enhances the usefulness of the AED 110, as well as realizing additional information request button 128 states of NOT PRESSED, PRESSED WHEN ILLUMINATED, and PRESSED WHEN NOT ILLUMINATED. If button press time states are used, as outlined above, illumination of information request button 128 will generally occur only if a "PRESSED <2 SECONDS" state has a corresponding message available.

Table 1 illustrates an exemplary set of context-sensitive user instructions which are issued in response to specific combinations of operational state and information request button states of "PRESSED <2 SECONDS", "PRESSED 2-TO-4 SECONDS", and "PRESSED >4 SECONDS". In this case, a cartridge containing rescue electrodes is installed in the AED 110. Exemplary operational states which are sensed by controller 120 with input from electrode interface 114 are "On, Pads Off", "On, Placing Pads", "On, Pads On, Analyzing", "On, Pads On, CPR Pause, CPR sensed", "On, Pads On, CPR Pause, CPR not sensed", "Standby, Self-Test OK", and "Standby, Self-Test Not OK". A brief description of the user information available at each state combination follows.

"On, Pads Off"—AED 110 activated with no user manipulation of stored electrode pads. In this operational state, a rescue has generally begun, and it is undesirable to distract the first-response user with information beyond the first tier voice prompting protocol. However, a second responder rescuer, presumably with a higher level of lifesaving skill, would have access to a "handoff" message which indicates the progress of the rescue. An exemplary handoff message is, "<number> shocks, <number> minutes" of operation, and might be available only if the information request button 128 is intentionally held down for 2 seconds or more. In this instance, and to avoid distracting the first-response user, the information request button would remain unilluminated, yet would still respond to the request of an operator who had received more extensive and advanced training and knows that this "hidden" information is available if needed.

"On, Placing Pads"—AED 110 activated with concurrent manipulation of electrode pads, but both pads are not affixed to the patient. Like the "On, Pads Off" operational state, it is undesirable to distract the first-response user with information beyond the first tier voice prompting protocol during this especially critical step in the rescue. A second responder rescuer, presumably with a higher level of lifesaving skill, again would have access to the "handoff" message which indicates the progress of the rescue prior to her arrival.

"On, Pads On, Analyzing"—AED 110 activated with both electrode pads affixed to the patient. AED 110 is analyzing the patient ECG and delivering defibrillation therapy if so determined. No detailed level of user information is necessary during this operational state.

"On, Pads On, CPR Pause, Initiate CPR"—AED 110 operational state is a CPR period as defined by a CPR treatment protocol, generally following the "On, Pads On, Analyzing" operational state, and when conditions indicate that CPR may be initiated. During the CPR pause, the rescuer is expected to provide CPR to the victim if the victim's condition warrants. Many rescuers are not proficient in the correct CPR protocols, including airway management, where to place hands, and the sequence and cadence of chest compressions and rescue breaths. Thus, during this period, a momentary press of the user information request button 128 will initiate instructions that will guide the user through the proper CPR procedure. Input indicator 132 may further prompt the user that this information is available by illuminating the button 128 accompanied by a standard voice protocol message saying "For help with CPR, press the illuminated button". Because this CPR information can be relatively extensive, it is made optionally available through the second-tier request. Likewise, if CPR is not indicated, the rescuer is not bombarded by CPR instructions that are distracting and introduce confusion as to whether or not CPR should be performed or withheld. A more proficient rescuer can thus be spared the distraction of extraneous CPR instructions and proceed with the rescue faster. Also, as in operational states 1 and 2 above, the second responder rescuer has access to the "handoff" message by holding the illuminated information request button down for 2 seconds or more.

"On, Pads On, CPR Pause, do not initiate CPR"—AED 110 operational state is a protocol-defined CPR period and when conditions indicate that CPR should not be initiated. In this case, the rescuer has perhaps panicked, or has not heard a post-analysis prompt saying that "It is safe to touch the patient" and has waited a significant period of time before requesting CPR assistance. When the information request button 128, again preferably illuminated, is pressed momentarily, the controller 120 delivers a message intended to reassure the user, such as "It is safe to touch the patient", but will not provide CPR instruction. A reason for withholding instruction is that the cumulative elapsed time from the start of the CPR pause to the press of the information request button 128 and then to the conclusion of the round of "instructed" CPR may exceed the recommendations of CPR treatment protocols. For example, if CPR protocol dictates a ninety second maximum CPR pause and the AED CPR prompting sequence consumes sixty seconds, then the "On, Pads On, CPR Pause, do not initiate CPR" operational state would begin 30 seconds after the beginning of the CPR pause, and last until the end of the CPR pause. Thus, an operator who delays requesting assistance for a significant period of time is not confused by abbreviated or interrupted CPR prompts. As in previous operational states, the second responder rescuer also has access to the "handoff" message by holding the illuminated information request button down for 2 seconds or more.

"Standby, Self-Test OK"—AED 110 is in standby or has been inadvertently turned off during rescue, and the most recent AED self-test indicates "OKAY". Assuming the more severe case of the AED 110 being inadvertently deactivated during a rescue, the information request button 128 when pressed, prompts the user to "In case of emergency, press the on/off button". This operational state also provides the handoff instruction for button 128 presses of 2 seconds or more, again for second tier responder purposes.

"Standby, Self-Test Not OK"—AED 110 is in standby or has been inadvertently turned off during rescue, and the most recent AED self-test indicates "NOT OKAY". Anytime the AED 110 is inactive and in a non-operational state, the buzzer 32 makes a periodic audible signal and concurrently the information request button 128 illuminates. When pressed, AED 110 prompts the user with the self-test failure corrective action. This gives the user the opportunity to quickly address the situation and resume the rescue. Exemplary self-test corrective action messages are: "Replace battery immediately" and "Pads not usable, insert new pads cartridge". This operational state also provides the handoff instruction for button 128 presses of 2 seconds or more, again for second tier responder purposes.

The electrode cartridge detection feature of the present invention has additional utility by discerning when no cartridge is present in the AED. Table 2 illustrates an exemplary set of user instructions which are issued in response to specific combinations of operational state and information request button states of "PRESSED <2 SECONDS", "PRESSED 2-TO-4 SECONDS", and "PRESSED >4 SECONDS" with no cartridge installed. Applicable operational states with no cartridge installed are: "On, Pads Off", "Standby, Self-Test OK", and "Standby, Self-Test Not OK". A brief description of the user information available at each state combination follows.

"On, Pads Off"—AED 110 activated with no electrode cartridge installed. If a rescue is intended in this operational state, a first-tier voice message automatically informs the user to install a cartridge, without requiring the push of the infor-

TABLE 1

Rescue Cartridge Installed

| | Operational State | | | | | | |
|---|---|---|---|---|---|---|---|
| I-Button State | On, Pads Off | On, Placing Pads | On, Pads On, Analyzing | On, Pads On, CPR Pause, Initiate CPR | On, Pads On, CPR Pause, Do Not Initiate CPR | Standby, Self-Test OK | Standby, Self-Test Not OK |
| Pressed <2 Sec. | None | None | None | Detailed CPR Handoff | Assure User Handoff | Initiate | Fail Type Handoff |
| Pressed 2-4 Sec. | Handoff | Handoff | None | Handoff | Handoff | Handoff | Handoff |
| Pressed >4 Sec. | None | None | None | None | None | Handoff | Handoff |

If controller 120 is disposed to detect the cartridge installed in AED 110 through electrode interface 114, additional instruction sets which depend upon operational state, button state, and cartridge type are contemplated. One apparatus for detecting a cartridge type is disclosed in the co-pending application XXXXXX titled "YYYY", Philips Invention Disclosure 704238, "Four Contact Identification System for Defibrillator Electrode Package, by Jonsen. In a first example, a rescue cartridge can be either an ADULT or PEDIATRIC rescue cartridge. Because CPR protocols differ substantially between adults and infants, controller 120 causes instruction generator 122 to select the appropriate CPR protocol depending on detected cartridge type. The "On, Pads On, CPR Pause, Initiate CPR" operational state accompanied by a momentary press of the information request button 128 would then prompt the appropriate ADULT or PEDIATRIC set of detailed CPR instructions.

The electrode cartridge detection feature of the present invention has additional utility by discerning when the AED is used in a non-rescue operational state. If the AED has a built-in training operational state, the training electrode cartridge should be disposed such that it cannot deliver a shock to a trainee or training mannequin. In the training operational state, the information request button 128 pressed momentarily would provide a means to select among a plurality of training scenario settings, or might optionally be used to select an alternate training scenario declaration. Such a feature is especially useful in an AED without a visual display.

mation request button. In this state, it is undesirable to distract the first-response user with information beyond that pertaining to cartridge installation since proceeding further with the rescue process is irrelevant without an installed electrode pads cartridge. Then, when a cartridge is installed per the automatic instruction, AED 110 reverts to the Table 1 information protocol. Absence of a cartridge in AED 110 can also signal controller 120 to operate in an administrational mode, said signal confirmed by pressing the information request button for more than 4 seconds. The sequence of removing the cartridge, activating AED 110, and then holding the information request button 128 would be well known to a routine user. Entry into the administration mode is accompanied by an "Administration" or equivalent voice prompt. The information request button 128 can then be manipulated to further advance through the various administration mode features, with additional voice prompting as appropriate.

"Standby, Self-Test OK"—The cartridge is absent AED 110 while in standby, and the most recent AED self-test indicates "OKAY". If the AED 110 is inactivated during the rescue and the cartridge is concurrently removed from AED 110, buzzer 32 makes a periodic audible signal and the information request button 128 simultaneously illuminates. When the information button is pressed momentarily, the AED 110 prompts the user to "In case of emergency, press the on/off button", followed closely by a prompt to insert a cartridge. This instruction is especially important in an AED with no graphical or text display, because it may not be apparent to the user that the AED has been inactivated and that the cartridge is not installed. The presence of a single illuminated information request button 128 will attract the user's attention and get the rescue back on track. In the more likely case of the cartridge removal occurring during the routine standby mode, AED 110 automatically indicates by some means, such as illuminated LED or audible beep sounds, that the AED 110 is not ready for use and that an operator or other maintenance individual needs to provide it with service. This feature spares battery life and environmental noise clutter by making more detailed cartridge insertion prompting dependent on the press of the information request button 128. This operational state also provides the handoff instruction for button 128 presses of 2 seconds or more, assuming that second responders have arrived, have inactivated the AED 110 and removed the cartridge, but still need pre-arrival rescue information. For button presses of 4 seconds or longer AED 110 will begin the administration mode as described in the previous paragraph.

"Standby, Self-Test Not OK"—The cartridge is absent AED 110 while in standby, and the most recent AED self-test indicates "NOT OKAY". Assumptions and response of the AED 110 to operational state and information request button 128 states are the same as for "Standby, Self-Test OK" operational state.

It should be appreciated that the scope of the invention is not limited to the embodiments described above. The above-described AED provides a second, more detailed layer of help information that is appropriate to both the operational, i.e. rescue, state and to an explicit user request. Such an AED can be modified and altered by those skilled in the art without departing from the spirit and scope of the present invention.

TABLE 2

| | No Cartridge Installed | | | | | | |
|---|---|---|---|---|---|---|---|
| | Operational State | | | | | | |
| I-Button State | On Pads Off | On Placing Pads | Pads On, Analyzing | On Pads On CPR, Initiate CPR | On Pads On CPR, Do Not Initiate CPR | Standby OK Self-Test | Standby Failed Self-Test |
| Pressed <2 Sec. | None | NA | NA | NA | NA | Insert Cartridge | Insert Cartridge |
| Pressed 2-4 Sec. | None | NA | NA | NA | NA | Handoff | Handoff |
| Pressed >4 Sec. | Admin | NA | NA | NA | NA | Admin | Admin |

What is claimed is:

1. An automated external defibrillator comprising:
   a single information request input control;
   a state parameter indicative of the current operational state of the defibrillator;
   an output; and
   a controller which provides context-sensitive rescue information to the output in response to the actuation of the information request input control and the current operational state of the defibrillator.

2. The automated external defibrillator of claim 1, further comprising a second state parameter indicating the defibrillator electrode status, wherein said controller further provides said context-sensitive rescue information based on said second state parameter.

3. The automated external defibrillator of claim 2, wherein said defibrillator electrode status comprises a rescue electrode status, training electrode status or electrode not installed status.

4. The automated external defibrillator of claim 3, wherein said rescue electrode status further comprises an adult electrode status or pediatric electrode status.

5. The automated external defibrillator of claim 1, wherein said state parameter is responsive to an impedance between electrodes which is indicative of said operational state of the defibrillator.

6. The automated external defibrillator of claim 1, wherein said context-sensitive rescue information comprises a CPR instruction.

7. The automated external defibrillator of claim 1, wherein said output is a speaker.

8. The automated external defibrillator of claim 1, wherein the information request input control is a button.

9. The automated external defibrillator of claim 8, wherein said button is selectively activated by said controller, and wherein said activation is indicated by the automated external defibrillator.

10. A method for operating the automated external defibrillator of claim 1 to provide context-sensitive rescue information to the user of the automated external defibrillator, the method comprising the steps of:
    requesting help through the single information request input control;
    determining the current operational state of the defibrillator by the defibrillator; and
    conveying through an output rescue information based on said requesting step and determining step.

11. The method of claim 10, further comprising the step of detecting a defibrillator electrode status, and wherein said rescue information is further based on said detecting step.

12. The method of claim 11, wherein said defibrillator electrode status comprises a rescue electrode status, training electrode status or electrode not installed status.

13. The method of claim 12, wherein said rescue electrode status further comprises an adult electrode status or pediatric electrode status.

14. The method of claim 11, wherein detecting a defibrillator electrode status further comprises the step of measuring an impedance between electrodes, and wherein said output rescue information is further based on said measuring step.

15. The method of claim 10, wherein said rescue information comprises a CPR instruction.

16. The method of claim 10, wherein said output is a speaker.

17. The method of claim 10, wherein said information request input control is a button.

18. The method of claim 17, further comprising the steps of:
- selectively activating said button based on said operational state; and
- illuminating said button in response to said activating step.

19. The method of claim 10, wherein said rescue information comprises one of defibrillator condition, defibrillation procedure guidance, user reassurance comments, enhanced CPR guidance, or defibrillator administrative guidance.

20. The automated external defibrillator of claim 1, wherein said rescue information further comprises one of defibrillator condition, defibrillation procedure guidance, user reassurance comments, enhanced CPR guidance, or defibrillator administrative guidance.

* * * * *